US012653355B2

(12) United States Patent
Nolte et al.

(10) Patent No.: US 12,653,355 B2
(45) Date of Patent: Jun. 16, 2026

(54) HYGIENIC PROCESS FOR AN AIR SUPPLY SYSTEM

(71) Applicant: STIEBEL ELTRON GMBH & CO. KG, Holzminden (DE)

(72) Inventors: Hubert Nolte, Hoexter (DE); Frank Stiebel, West Hatfield, MA (US)

(73) Assignee: Stiebel Eltron GmbH & Co. KG, Holzminden (DE)

( * ) Notice: Subject to any disclaimer, the term of this patent is extended or adjusted under 35 U.S.C. 154(b) by 780 days.

(21) Appl. No.: 17/983,903

(22) Filed: Nov. 9, 2022

(65) Prior Publication Data

US 2023/0142979 A1 May 11, 2023

(30) Foreign Application Priority Data

Nov. 10, 2021 (DE) .......................... 102021129184.4

(51) Int. Cl.
*A61L 9/20* (2006.01)
*A47K 10/48* (2006.01)

(52) U.S. Cl.
CPC ................ *A47K 10/48* (2013.01); *A61L 9/20* (2013.01); *A61L 2209/111* (2013.01); *A61L 2209/12* (2013.01)

(58) Field of Classification Search
CPC ....................................................... A61L 9/20
See application file for complete search history.

(56) References Cited

U.S. PATENT DOCUMENTS

| | | | | |
|---|---|---|---|---|
| 2021/0369881 A1* | 12/2021 | Hayden | ................. | A61L 2/0023 |
| 2022/0125986 A1* | 4/2022 | Shalvi | ................ | B01D 46/0028 |
| 2022/0268462 A1* | 8/2022 | Sasonov | ................... | A61L 9/20 |

FOREIGN PATENT DOCUMENTS

| | | | | | |
|---|---|---|---|---|---|
| CN | 111648980 A | * | 9/2020 | ............. | A61L 9/205 |
| DE | 102017009637 A1 | | 5/2019 | | |
| DE | 202018001847 U1 | | 7/2019 | | |
| DE | 102020119225 B3 | | 10/2021 | | |
| DE | 102020125106 A1 | | 3/2022 | | |
| EP | 2656762 A2 | | 10/2013 | | |

OTHER PUBLICATIONS

English Translation of Document Identification No. CN 111648980 A provided by the United States Patent and Trademark Office Search Tool Search: Chen, Lian-yan; Internal Sterilizing Fan and Fan with Sterilizing Function; Sep. 11, 2020 (Year: 2020).*

* cited by examiner

*Primary Examiner* — Kevin Joyner
(74) *Attorney, Agent, or Firm* — Brooks Kushman P.C.

(57) ABSTRACT
The invention relates to an air blower apparatus, in particular a jet air hand dryer, comprising: a housing having an inlet and an outlet, at least one air duct extending inside the housing between the inlet and the outlet, for guiding an air stream, a fan unit for producing a directed stream of air in the air duct, and a UV treatment unit arranged inside a section of the air duct, said UV treatment unit having a treatment chamber for at least parts of the stream passing through the air duct, characterised in that the treatment chamber is at least part of a receiving chamber for a fan impeller in the fan unit, wherein a plurality of lighting adapted to emit UV light are arranged inside the receiving chamber.

20 Claims, 2 Drawing Sheets

HYGIENIC PROCESS FOR AN AIR SUPPLY SYSTEM

CROSS-REFERENCE TO RELATED APPLICATIONS

This application claims priority to German Patent Application No. DE 102021129184.4 filed Nov. 10, 2021, the disclosure of which is hereby incorporated in its entirety by reference herein.

TECHNICAL FIELD

The invention relates to an air blower apparatus, in particular, to a jet air hand dryer.

BACKGROUND

Air blower apparatuses are used in air handling systems, for example, to ventilate rooms in buildings. Such air blower apparatuses are used to control the exchange of air inside a room, thus also allowing the climatic conditions in the room to be adjusted at the same time. Such air blower apparatuses are also used in the sanitary field as jet air hand dryers, which deliver a stream of air used to dry hands.

An air blower apparatus having a base member with an air inlet and an air outlet is known, for example, from DE 20 2018 001 847 U1, in which a treatment chamber is provided between the air inlet and the air outlet. A UV treatment unit for disinfecting the air stream passing through the air blower apparatus is arranged inside the treatment chamber.

A hand dryer having a housing is also shown in DE 10 2017 009 637 A1, for example. A hollow space which is accessible from the outside through a housing opening is provided in the housing, for receiving hands to be dried, onto which a stream of air produced by a fan is directed. Also arranged inside the hollow space is a device for producing UV radiation, which is designed to emit UV radiation for disinfecting hands that are inserted into the hollow space.

Described herein is an air blower apparatus and also a method of disinfecting an air stream passing through an air handling system, by means of which an air stream passing through the air blower unit is disinfected efficiently and above all in a permanently reliable manner.

SUMMARY

An jet air hand dryer may include a housing having an inlet and an outlet, at least one air duct extending inside the housing between the inlet and the outlet, for guiding an air stream, a fan unit for producing a directed stream of air in the air duct, and a UV treatment unit arranged inside a section of the air duct, said UV treatment unit having a treatment chamber for at least parts of the stream passing through the air duct. Also disclosed is a method of disinfecting an air stream passing through an air handling system.

According to a first aspect, an air blower apparatus, such as jet air hand dryer, may include a housing having an inlet and an outlet. At least one air duct extends inside the housing between the and the outlet for guiding an air stream. A fan unit produces a directed stream of air in the air duct. The apparatus further includes a UV treatment unit arranged inside a section of the air duct. The UV treatment unit has a treatment chamber for at least parts of the air stream passing through the air duct. The treatment chamber is at least part of a receiving chamber for a fan impeller in the fan unit, wherein a plurality of UV light sources are arranged inside the receiving chamber. In some embodiments, the treatment chamber through which at least parts of the air stream flow through the air duct is part of a receiving chamber for a fan impeller in the fan unit, wherein a plurality of lighting means adapted to emit UV light are arranged inside the receiving chamber.

The in the disclosed approach, disinfection is not limited, due to the UV treatment unit, only to at least parts of the air passed through the air blower apparatus, and thus an arbitrary section of the air blower apparatus, but that disinfection with UV light is performed in a special section of the air blower apparatus. For example, disinfection of parts of the air stream and of the air blower apparatus is carried out in the region that the air stream must inevitably pass through when the directed and forced air stream is produced by the air blower apparatus. This results in efficient, and above all, permanently reliable disinfection in the region, namely in the fan unit, that comes into contact with the air stream over a relatively large area. In addition to the air stream itself, regions of the fan unit, particularly surfaces of the fan unit, may also disinfected by the UV light.

According to an example embodiment of the invention, the lights of the UV treatment unit are directed in the receiving chamber towards the fan impeller. As a result, the UV light may be directed towards the part of the fan unit that is used to produce the air stream inside the air blower apparatus. The fan impeller, for example, which is the component of the air blower apparatus that comes into contact over a relatively large area with the air stream passed through the air blower apparatus, is thus exposed to UV light and therefore disinfected. Exposing the fan impeller to UV light further improves the disinfection effect achieved by the air stream passed through the air blower apparatus.

According to another embodiment, the lighting sources are directed towards an outer circumferential surface of the fan housing such that the UV light emitted by the lighting sources hits the surfaces of the fan impeller vanes and/or radiates into the interspaces between the fan impeller vanes. By pointing the lighting sources at the outer circumferential surface of the fan impeller, a large proportion of the UV light emitted by the lighting sources of the UV treatment unit reaches almost the entire surface of the fan impeller. The disinfection effect is further improved as a consequence.

In a yet another embodiment, the lighting sources are arranged on a curved path, e.g., a circular path, around an outside of the fan impeller and radiate in the direction of a center point defined by the curved path. This arrangement has the effect that the fan impeller vanes of the fan impeller are exposed, in some instances over their entire surface, to the UV light. The lighting sources may be arranged on the circular path around the outside of the fan impeller in such a way that the interspaces between the fan impeller vanes are also completely irradiated. When the fan impeller rotates and the air stream is produced, the entire surface of the fan impeller conveying the air stream may be exposed to UV light of the UV treatment unit and the interspaces completely irradiated at the same time. The disinfection effect achieved by the UV treatment unit may be increased as a result.

The fan unit may be a centrifugal fan, and the lighting sources are preferably arranged at intervals (spaced apart) from one another on a circumferential surface of the receiving chamber surrounding the fan impeller on its outside. By providing a centrifugal fan, it is possible to combine in an advantageous manner the irradiation of the surface of the fan impeller vanes and also the irradiation of the air stream flowing radially outwards between the fan impeller vanes. The lighting may be arranged at intervals along the circumferential surface of the receiving chamber for the fan impeller, whereby at least a quarter, or more than half, of the outer circumferential surface of the receiving chamber surrounding the fan impeller is fitted with lighting sources. At least half of the surface of the stationary fan impeller may be exposed to the UV light that produces the disinfection effect.

The receiving chamber may be substantially cylindrical in shape, and the fan impeller may be arranged off-center in the receiving chamber. The lighting sources may be arranged, at increasingly large intervals in the direction of the outlet, on the circumferential surface of the receiving chamber encasing the fan impeller. Due to the off-center arrangement, the distance between the circumferential surface of the fan impeller and the circumferential surface of the receiving chamber surrounding the fan impeller gradually widens, with the largest distance being found in the region of the outlet. As the distance of the circumferential surface of the receiving chamber from the circumferential surface of the fan impeller increases, the selected distance between the lighting sources arranged on the circumferential surface can be greater, because with increasing distance from the outer circumferential surface of the fan impeller, the surface area irradiated by the light emitted from the lighting means onto the fan impeller increases. The distance between the outer circumferential surface of the receiving chamber and the circumferential surface of the fan impeller is preferably smallest in the transition region between the outlet and the housing portion that then adjoins in the direction of rotation of the fan impeller.

According to a development of the air blower apparatus, the lighting sources are designed to emit light with a wavelength in the UV-C range from 100 nm to 280 nm. The lighting sources may be UV lights, e.g., UV-C light emitting diodes (LED), that may be arranged in electrical communication with each other on a flexible strip of material. A simple way of producing the UV light is to provide UV-C diodes as the lighting sources, by means of which the fan impeller and the air stream passing through the air blower apparatus can be disinfected. Using diodes also results in a long service life of the lighting means, thus resulting in low-maintenance operation of the air blower apparatus.

The UV-C light emitting diodes may emit light with a wavelength ranging from 100 nm to 280 nm, such as in the range of 200 nm to 280 nm, in the range between 240 nm and 270 nm, or with a wavelength of about 254 nm. In the present case, "about" should be understood as the UV light being emitted in the range of 254 nm+/−5%. The above specifications are to be understood here to mean that, light is emitted by means of the UV-C diodes predominantly in the specified range, whereby lower intensity light may also be emitted in adjacent regions.

According to a further embodiment of the air blower apparatus, the housing has at least two housing portions, wherein the two housing portions are connected sealingly to each other a strip of material. The multi-part housing design simplifies installation of the air blower apparatus, in that, components of the air blower apparatus to be arranged accordingly inside the housing can be easily inserted into a housing that consists of two half-shells, for example.

The housing of the air blower apparatus may be consisting of at least two housing portions that is sealed by means of a flexible strip of material so that the UV light produced inside the treatment chamber of the UV treatment unit is prevented from escaping from the interior of the treatment chamber of the air blower apparatus. In one embodiment, the flexible strip of material is the strip of material on which the lights are arranged in electrical communication with each other. The flexible material strip may also form a part of the receiving chamber encasing the circumferential surface of the fan impeller on its outside.

According to an example embodiment of the air blower apparatus, at least the treatment chamber inside the air duct has a material that reflects the UV light emitted from the lighting sources. For example, parts of the receiving chamber for the fan impeller and also, where relevant, the fan impeller itself are lined with a reflective material or coated with a paint that reflects UV light. With the aid of the reflective material, reflection inside the housing and/or by the surface of the fan impeller is multiply increased, so the UV light is increased in intensity and can reach regions of the fan unit that are not irradiated directly by the lighting sources of the UV treatment unit. Increased reflection also results in a further improvement in the disinfection effect on the air stream conducted through the apparatus and on the fan impeller in an air blower apparatus designed in this way. A reflective foil, for example, can be applied as the reflective material to the inner side of the fan unit housing portions forming the receiving chamber. In an alternative embodiment, the reflective material can be applied to the housing and/or the surface of the fan impeller in the form of a coating on the inner side of the receiving chamber. In another alternative embodiment, the fan impeller and the housing surrounding the fan impeller may be made of anodized aluminum, with the inner side consisting of polished material to improve its reflective properties.

According to another example embodiment, the air blower apparatus further includes a heating device for heating the air stream flowing through the air duct and/or a detection means associated with the outlet at the air duct, comprising at least one sensor for sensing at least the presence of an object approaching the outlet. With the aid of the heating device, the air stream flowing through the air duct can be heated in a simple manner. In an air blower apparatus used as a jet air hand dryer, the drying effect produced by the air discharged from the outlet of the air blower apparatus can be improved by the heated air stream.

With the aid of a detection means (e.g., a proximity detector or motion sensor) associated with the outlet of the air duct, which may have at least one sensor for sensing at least the presence of an object approaching the outlet, when the presence of the detected object is sensed, at least the fan unit is switched on so as to produce an air stream discharged from the outlet of the air blower apparatus.

If an object moves out of the detection range of the detection means, i.e., is no longer sensed by the sensor of the detection means, the air blower apparatus is configured to switch OFF, such as after a predetermined stopping time, at least the fan unit for producing the air stream and also, where applicable, the UV treatment unit previously switched on concurrently.

The sensor of the detection means may be embodied as a photodiode, for example.

According to one embodiment of the disclosure, the air blower apparatus includes a control unit for controlling at least one drive means that drives the fan impeller, the heating device and/or the treatment unit. The control unit may be coupled in electric communication with the detection means and/or with at least a signal receiving means. In a preferred embodiment, the drive means for the fan impeller, the heating device and also the treatment unit are controlled with the aid of the control unit. The control unit can may be used to adjust different processes or programs on the air blower apparatus, with which one, two, or all three components can be controlled simultaneously as required.

According to a development of the disclosure, the control unit is coupled to a detector that includes a sensor that detects whether an object is approaching the outlet of the air blower apparatus. The control unit may be coupled in electric communication with a signal receiver, such that the air blower apparatus can be activated by a separate portable communication device, such as a mobile communication device, that communicates with the signal receiver. In addition to the programs stored permanently in the control unit, a query or targeted activation for performing a function check on the air blower apparatus can be transmitted to or carried out on the control unit by a person responsible for maintenance. In addition, further additional functions or programs can also be transmitted to the control unit and stored in its memory via the signal receiving device.

According to a second aspect, a method of disinfecting an air stream passing through an air handling system is disclosed. An air blower apparatus according to any of the above-described embodiments described above is arranged inside the air handling system.

The disclosure thus proposes a method of disinfecting an air stream passing through an air handling system, in which the air stream to be produced is disinfected inside the components that are primarily involved in producing the forced flow of air. Furthermore, in comparison with the other components of the air handling system, and due to its rotational movement, a significantly greater proportion of the fan unit, e.g., the fan impeller, comes into contact with the air conducted through the air blower apparatus than is the case with any sections of the air duct in the air blower apparatus extending upstream or downstream from the fan unit. The fan unit thus poses a correspondingly high risk of contamination for the air passing through it, which is counteracted with the method according to the invention by UV light being emitted by a plurality of lighting sources arranged inside the receiving chamber for the fan impeller of the fan unit. For example, the UV-C light produced by means of the lighting means is emitted onto the outer circumferential surface of the fan impeller and thus onto the surface of the fan impeller vanes and into the interspaces between the fan impeller vanes.

According to one embodiment, a method includes one or more or all of the following steps: driving the fan impeller and simultaneously actuating the lighting sources to produce a UV light for disinfecting an air stream flowing through an air duct; driving the fan impeller and simultaneously actuating the lighting sources to produce the UV light for disinfecting the air stream flowing through the air duct and actuating a heating device for heating the air stream; driving the fan impeller and simultaneously actuating the lighting source to produce the UV light for disinfecting the air stream flowing through the air duct and actuating a heating device for heating the air stream for a specified period of time, wherein, after the specified period of time has elapsed, the heating device is switched OFF and the fan impeller is driven at a reduced speed with the lighting sources still switched ON, and actuating the lighting sources to produce the UV light for disinfecting the fan impeller when the fan impeller is stationary. Different operating modes can be run on the air blower apparatus by applying the various steps listed above. For example, if the fan unit is switched OFF and the lighting sources for producing the UV light is switched ON, disinfection is performed solely on the interior of the air blower apparatus.

All other operating modes in which the fan impeller rotates and a directed air stream from the inlet towards the outlet is produced and the air blower apparatus is used, in particular, as a jet air hand dryer, the air stream produced is dispensed onto an object which is brought into the proximity of the outlet, such as a pair of hands to be dried. Due to the disinfection process carried out inside the air blower apparatus, the air stream produced is almost free of harmful or health-endangering elements, such as pathogens.

The embodiments and developments of the air blower apparatus according to the first aspect of the invention are at the same time also embodiments of the method according to the second aspect of the invention, insofar as they should not contradict each other. The embodiments and developments described with reference to the second aspect of the invention are at the same time also embodiments of the air blower apparatus according to the first aspect.

DETAILED DESCRIPTION

Figure 1:
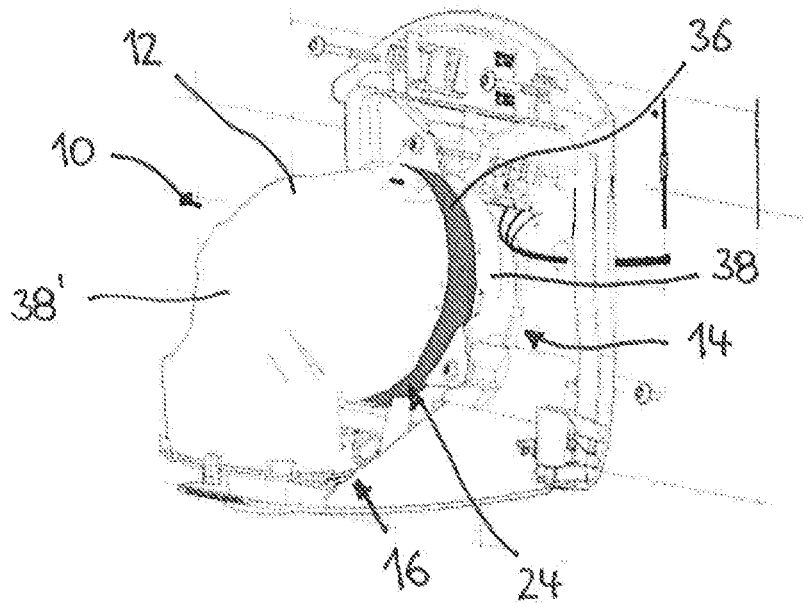
FIG. 1 shows a perspective view of a first embodiment of an air blower apparatus according to the disclosure.

FIG. 1 shows an air blower apparatus, such as a jet air hand dryer for producing a forced air stream. Air blower apparatus 10 includes a housing 12 having an inlet 14 and an outlet 16 and an air duct extending inside housing 12 between inlet 14 and outlet 16. A fan unit 20 is arranged inside housing 12 and has a fan impeller 22 that circulates an air stream 23 in air duct 18 from the inlet in the direction of the outlet.

Air blower apparatus 10 also includes a UV treatment unit 24 that is arranged inside a section of air duct 18. The UV treatment unit includes a treatment chamber 26 for at least parts of the air stream 23 passing through air duct 18.

In the embodiment shown in FIG. 1, the treatment chamber 26 is part of a receiving chamber for the fan impeller 22 of fan unit 20. A plurality of lighting sources 30 designed to emit UV light are arranged inside receiving chamber 28.

Figure 2:
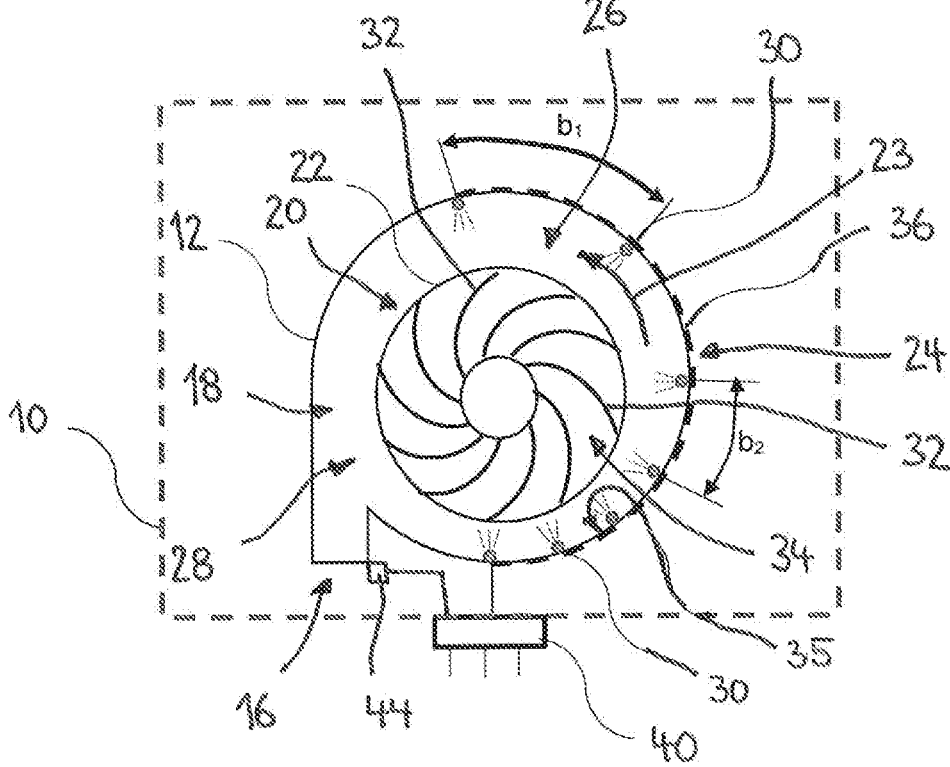
FIG. 2 shows a schematic view of the air blower apparatus shown in FIG. 1, in cross-section.

As illustrated in FIG. 2, the lighting sources 30 in receiving chamber 28 for the fan impeller are aimed directly at fan impeller 22. Fan impeller 22 has a plurality of fan impeller vanes 32 and interspaces 34 between adjacent fan impeller vanes, through which air drawn in, in particular in the center of fan impeller 22, is transported radially to the outside. In the present embodiment, fan unit 20 is designed as a centrifugal fan.

Lighting sources 30 are aimed at the outer circumferential surface of the fan impeller in such a way that the UV light emitted by lighting sources 30 radiates onto the surfaces of fan impeller vanes 32 and into the interspaces 34 between fan impeller vanes 32. To ensure uniform irradiation of the fan impeller with UV light inside receiving chamber 28, which forms a section of air duct 18, the lighting sources are arranged at intervals from one another on the circumferential surface of the receiving chamber surrounding fan impeller 22 on its outside.

In the embodiment shown here, receiving chamber 28 is substantially cylindrical in shape, and fan impeller 22 is arranged off-center in receiving chamber 28. The air duct formed between the fan impeller and the outer side of the receiving chamber thus widens gradually in the direction of outlet 16. The radial distance between lighting sources 30 and the outer circumferential surface of fan impeller 22 changes, therefore, which is why lighting sources 30 are arranged on the circumferential surface 35 of receiving chamber 28 at widening intervals from each other in the direction of outlet 16.

The lighting sources are designed to emit light with a wavelength in the UV-C range from 100 nm to 280 nm, the lighting sources may be UV-C light emitting diodes.

In one embodiment, lighting sources 30 are arranged in electrical communication with each other on a flexible strip of material 36. As shown by way of example in FIG. 1, the flexible strip of material 36 with inwardly facing lights 30 arranged thereon may be arranged between two housing portions 38, 38' of housing 12. In the embodiment shown in FIG. 1, the strip of material 36 seals the two housing portions 38, 38' to each other.

In one embodiment, the treatment chamber inside the air duct has a material that reflects the light emitted from lights 30, thus resulting in greater irradiation of the treatment chamber 26 of UV treatment unit 24. Air blower apparatus 10 also includes a control unit 40 for controlling a drive means 42 that sets fan impeller 22 in rotational motion, in particular, and/or for controlling UV treatment unit 24. Control unit 40 controls the switching ON and OFF of fan unit 20 and UV treatment unit 24. The drive means 42 may be a motor.

In the present embodiment, control unit 40 is coupled in electrical communication with a detector 44 including at least one sensor for sensing at least the presence of an object approaching outlet 16 of air blower apparatus 10.

Figure 3:
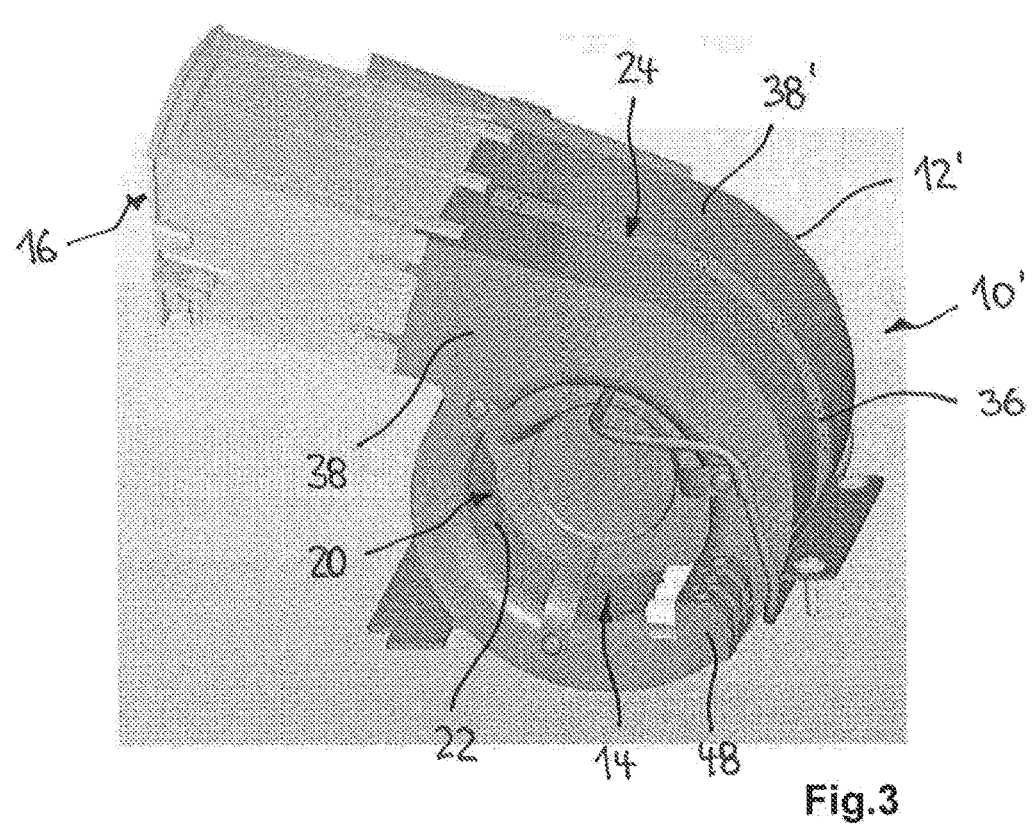
FIG. 3 shows a perspective view of another embodiment of an air blower apparatus according to the disclosure.

FIG. 3 shows another embodiment of an air blower apparatus 10' that includes a housing 12'. Housing 12' has an inlet 14 and an outlet 16 and an air duct 18 extending inside housing 12' between the inlet and the outlet. A fan unit 20 having the drive means 42 and a fan impeller 22 which can be set in rotational motion by the drive means is arranged in housing 12'.

Fan unit 20 is embodied for its part as a centrifugal fan. Air blower apparatus 10' includes a control unit, not shown in further detail, which is supplied with electrical power via a power connection 45.

Figure 4:
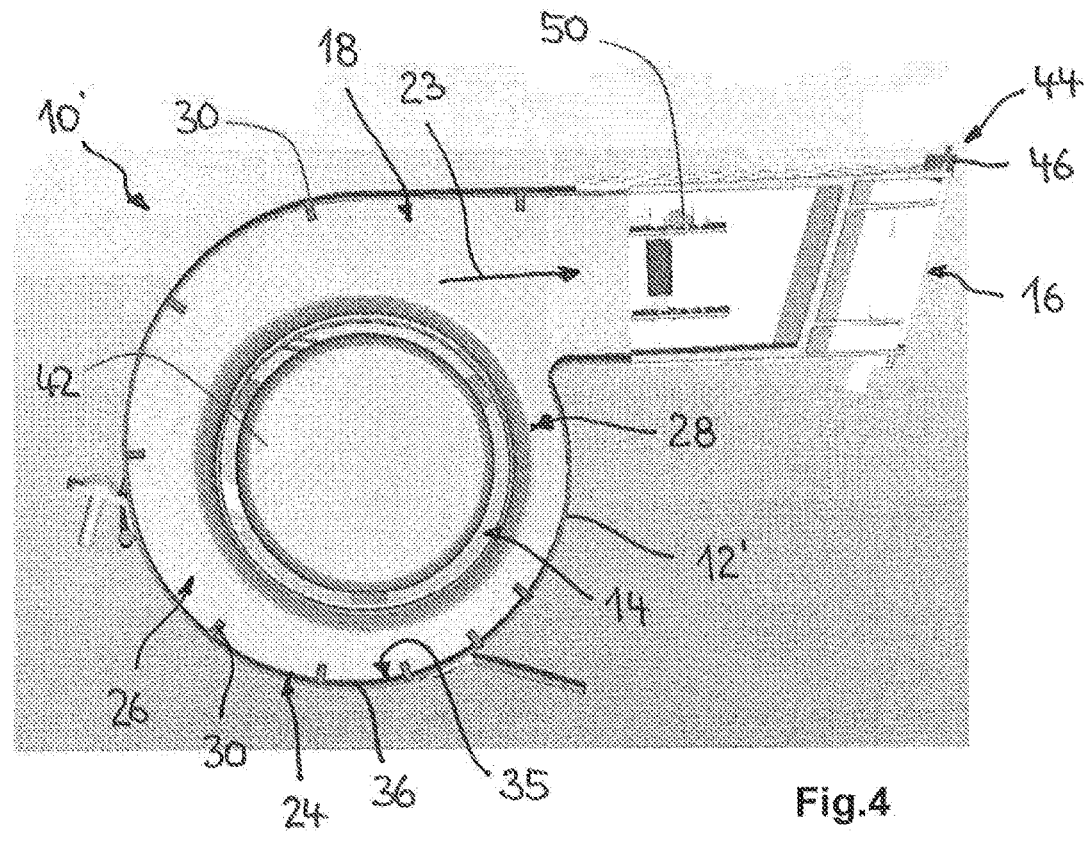
FIG. 4 shows a cross-sectional view of the air blower apparatus shown in FIG. 3.

Housing 12' also includes two housing portions 38, 38' which are connected sealingly to each other by a flexible strip of material 36, on which, in the embodiment shown here, lighting sources 30 (FIG. 4), embodied as UV-C diodes, are arranged in electrical communication with each other. As can be seen from the cross-sectional view in FIG. 4, fan unit 20 is arranged inside housing 12, which forms a receiving chamber 28 for the fan unit and an air duct 18 for the air stream conducted from inlet 14 to outlet 16.

In the embodiment shown here, a heating device 48 for heating the air stream 23 flowing through air duct 18 is provided in a section of the air duct. In one possible embodiment, a detector 44 having at least one sensor 46 is configured to sense at least the presence of an object approaching outlet 16 or associated with outlet 16 of air blower apparatus 10'.

Fan unit 20, e.g., its drive means 42, as well as heating device 50, and/or UV treatment unit 24 are controlled by the control unit of air blower apparatus 10', not shown here in further detail, if the presence of an object at outlet 16 is detected by the detector 44.

The control units of air blower apparatuses 10, 10' are configured to operate the air blower apparatus according to one or more of the following steps: driving fan impeller 22 and simultaneously actuating lighting sources 30 to produce the UV light for disinfecting the air stream 23 flowing through air duct 18; driving fan impeller 22 and simultaneously actuating lighting sources 30 to produce the UV light for disinfecting the air stream 23 flowing through the air duct 18 and actuating a heating device 50 for heating the air stream; driving fan impeller 22 and simultaneously actuating lighting sources 30 to produce the UV light for disinfecting the air stream flowing through air duct 18 and actuating a heating device 50 for heating air stream 23 for a specified period of time, wherein, after the specified period of time has elapsed, heating device 50 is switched OFF and fan impeller 22 is driven at a reduced speed with lighting sources 30 still switched ON, and actuating lighting sources 30 to produce the UV light for disinfecting the disinfecting fan impeller 22 when the fan impeller is stationary.

LIST OF REFERENCE SIGNS

10, 10' Air blower apparatus
12, 12' Housing
14 Inlet
16 Outlet
18 Air duct
20 Fan unit
22 Fan impeller
23 Air stream
24 UV treatment unit
26 Treatment chamber
28 Receiving chamber
30 Lighting source
32 Fan impeller vane
34 Interspace
35 Circumferential surface (receiving space)
36 Strips of material
38, 38' Housing portion
40 Control unit
42 Drive means
45 Power connection
44 Detector
46 Sensor
48 Power connection
50 Heating device

What is claimed is:
1. An air blower apparatus comprising:
a housing having an inlet and an outlet;
at least one air duct extending inside the housing between the inlet and the outlet and configured to guide an air stream;
a fan unit having a fan impeller configured to produce the air stream in the air duct; and
a UV treatment unit arranged inside a section of the air duct, the UV treatment unit having a treatment chamber for at least parts of the air stream passing through the air duct; wherein
the treatment chamber is at least part of a receiving chamber for the fan impeller in the fan unit, and a plurality of lights adapted to emit UV light are arranged inside the receiving chamber,
the lights are designed to emit light with a wavelength in a UV-C range from 100 nm to 280 nm, inclusive,
the lights are light emitting diodes (LEDs) and are arranged in electrical communication with each other on a flexible strip of material, and
the housing has at least two housing portions that are connected sealingly to each other by the strip of material.

2. The air blower apparatus according to claim 1, wherein the lights in the receiving chamber are directed towards the fan impeller.

3. The air blower apparatus according to claim 2, wherein the lights are directed towards an outer circumferential surface of the fan impeller such that the UV light emitted by the lights hits vanes of the fan impeller or radiates into interspaces between the vanes.

4. The air blower apparatus according to claim 3, wherein the fan unit is a centrifugal fan, and the lights are arranged at intervals from one another on a circumferential surface of the receiving chamber surrounding the fan impeller.

5. An air blower apparatus comprising:
a housing having an inlet and an outlet;
at least one air duct extending inside the housing between the inlet and the outlet and configured to guide an air stream;
a centrifugal fan unit having a fan impeller configured to produce the air stream in the air duct;
a UV treatment unit arranged inside a section of the air duct, the UV treatment unit having a treatment chamber for at least parts of the air stream passing through the air duct;
wherein the treatment chamber is at least part of a receiving chamber for the fan impeller in the fan unit; and
a plurality of lights adapted to emit UV light are arranged inside the receiving chamber and directed towards an outer circumferential surface of the fan impeller such that the UV light emitted by the lights hits vanes of the fan impeller or radiates into interspaces between the vanes, wherein the lights are arranged at intervals from one another on a circumferential surface of the receiving chamber surrounding the fan impeller;
wherein the receiving chamber is substantially cylindrical in shape, and the fan impeller is arranged off-center in the receiving chamber, wherein the lights are arranged on the circumferential surface at increasingly larger intervals in a direction of the outlet.

6. The air blower apparatus according to claim 5, wherein the lights are designed to emit light with a wavelength in a UV-C range from 100 nm to 280 nm, inclusive, wherein the lights are light emitting diodes (LEDs) and are arranged in electrical communication with each other on a flexible strip of material.

7. The air blower apparatus according to claim 6, wherein the housing has at least two housing portions that are connected sealingly to each other by the strip of material.

8. The air blower apparatus according to claim 1, wherein the treatment chamber inside the air duct has a material that reflects UV light emitted from the lights.

9. The air blower apparatus according to claim 1 further comprising a heating device configured to heat the air stream flowing through the air duct.

10. The air blower apparatus according to claim 1 further comprising a detector associated with the outlet of the air duct, the detector including at least one sensor configured to sense an object approaching the outlet.

11. The air blower apparatus according to claim 7 further comprising:
a control unit in electric communication with the detector and configured to control the fan impeller based on signals from the detector.

12. The air blower apparatus according to claim 9, wherein the treatment chamber inside the air duct has a material that reflects UV light emitted from the lights.

13. The air blower apparatus according to claim 9 further comprising a heating device configured to heat the air stream flowing through the air duct.

14. The air blower apparatus according to claim 9 further comprising a detector associated with the outlet of the air duct, the detector including at least one sensor configured to sense an object approaching the outlet.

15. The air blower apparatus according to claim 14 further comprising:
a control unit in electric communication with the detector and configured to control the fan impeller based on signals from the detector.

16. An air blower apparatus comprising:
a housing having an inlet and an outlet;
at least one air duct extending inside the housing between the inlet and the outlet and configured to guide an air stream;
a fan unit having a fan impeller configured to produce the air stream in the air duct;
a UV treatment unit arranged inside a section of the air duct, the UV treatment unit having a treatment chamber for at least parts of the air stream passing through the air duct, wherein the treatment chamber is at least part of a receiving chamber for the fan impeller in the fan unit; wherein the receiving chamber is substantially cylindrical in shape, and the fan impeller is arranged off-center in the receiving chamber; and
a plurality of lights adapted to emit UV light and arranged on a circumferential surface of the receiving chamber at increasingly larger intervals in a direction of the outlet.

17. The air blower apparatus according to claim 16, wherein the lights are designed to emit light with a wavelength in a UV-C range from 100 nm to 280 nm, inclusive, wherein the lights are light emitting diodes (LEDs) and are arranged in electrical communication with each other on a flexible strip of material.

18. The air blower apparatus according to claim 17, wherein the housing has at least two housing portions that are connected sealingly to each other by the strip of material.

19. The air blower apparatus according to claim 16, wherein the fan unit is a centrifugal fan.

20. The air blower apparatus according to claim 16 further comprising a heating device configured to heat the air stream flowing through the air duct.

* * * * *